United States Patent [19]

Meier et al.

[11] Patent Number: 5,436,370
[45] Date of Patent: * Jul. 25, 1995

[54] PROCESS FOR THE PREPARATION OF 3-NITROBENZENESULFONYL CHLORIDE

[75] Inventors: Michael Meier, Frankfurt am Main; Reinhard Wagner, Wiesbaden, both of Germany

[73] Assignee: Hoechst AG, Frankfurt, Germany

[*] Notice: The portion of the term of this patent subsequent to Aug. 4, 2009 has been disclaimed.

[21] Appl. No.: 924,034
[22] PCT Filed: Feb. 21, 1991
[86] PCT No.: PCT/EP91/00322
§ 371 Date: Sep. 2, 1992
§ 102(e) Date: Sep. 2, 1992
[87] PCT Pub. No.: WO91/13863
PCT Pub. Date: Sep. 19, 1991

[30] Foreign Application Priority Data

Mar. 3, 1990 [DE] Germany ............... 40 06 666.5

[51] Int. Cl.⁶ ............... C07C 303/08; C07C 303/12; C07C 309/86
[52] U.S. Cl. ............... 562/828; 562/830
[58] Field of Search ............... 562/828, 830

[56] References Cited

U.S. PATENT DOCUMENTS

| | | | |
|---|---|---|---|
| 3,574,739 | 4/1971 | Wei et al. | 260/556 |
| 4,166,070 | 8/1979 | Blank . | |
| 5,136,043 | 8/1992 | Meier et al. | 548/221 |

FOREIGN PATENT DOCUMENTS

| | | |
|---|---|---|
| 0289847 | 11/1988 | European Pat. Off. . |
| 0403947 | 12/1990 | European Pat. Off. . |
| 2360568 | 3/1978 | France . |
| 89997 | 7/1895 | Germany . |
| 1097613 | 6/1984 | U.S.S.R. . |

OTHER PUBLICATIONS

"The Organic Chemistry of Sulfur, Tetracovalent Sulfur Compounds", Chester Merle Suter, Wiley & Sons, Inc., New York, p. 223.
BIOS Final Report No. 1153, "I.G. Farbenindustrie. The Manufacture of Miscellaneous Dyestuff Intermediates (Excluding Naphthalene Derivatives)", British Intellegence Objectives Sub–Committee, London, pp. 38–39.
Chem. Abstract No. 104:68593s of Czechoslovkia 219,703.
Chem. Abstract No. 98:215331t of JP 57/203,056.
Chemical Abstracts, vol. 101, p. 613; abstract 210737a, & Su, A, 1097613 (Voroshilovgrad machine Building–Institute, Rubezhnoe) (1984).
Chemical Abstracts, vol. 113, No. 9; abstract 77909n, & JP, A, 02108661 (EIWA Chemical Industrial Co., Ltd) (1990).

*Primary Examiner*—Gary Geist
*Attorney, Agent, or Firm*—Connolly & Hutz

[57] ABSTRACT

In a method for preparing 3-nitrobenzene sulphonic acid chloride from nitrobenzene and chlorosulphonic acid, nitrobenzene is reacted with chlorosulphonic acid at approximately 90° to approximately 120° C. and an inorganic acid chloride is then allowed to act on the resultant reaction mixture at approximately 40° to approximately 90° C.

17 Claims, No Drawings

PROCESS FOR THE PREPARATION OF 3-NITROBENZENESULFONYL CHLORIDE

The invention relates to an improved process for the preparation of 3-nitrobenzenesulfonyl chloride in high yields by reaction of nitrobenzene with chlorosulfonic acid and subsequent action of an inorganic acid chloride.

3-nitrobenzenesulfonyl chloride is an important precursor, in particular for the preparation of dyes.

It is known (BIOS Final Report No. 1153, p. 38) that 3-nitrobenzenesulfonyl chloride can be prepared by sulfochlorination of nitrobenzene at temperatures of 60° C.–105° C. In this process, the nitrobenzene is added to 4 mol of chlorosulfonic acid, the temperature slowly rising to 60° C. After addition is complete, the reaction mixture is slowly heated to 70° C. and then up to 105° C. and finally kept several hours at 105° C. The yield in this process was given as 79% of theory, which is insufficient for a large-scale process. It is further known (C. M. Suter, "The Organic Chemistry of Sulfur", John Wiley & Sons Inc., New York/London, 1944, page 223), that on heating nitrobenzene with 2 mol equivalents of chlorosulfonic acid 3-nitrobenzenesulfonyl chloride is allegedly formed (which has been questioned again in more recent literature), violent decomposition of the reaction mixture occurring with the formation of $SO_2$ on heating at 150° C. for several hours.

The preparation of 3-nitrobenzenesulfonyl chloride by chlorination of 3-nitrobenzenesulfonic acid with chlorine/disulfur dichloride is likewise described (Chem. Abstr. 104 [1986] 68 593s). 3-Nitrobenzenesulfonyl chloride could also be prepared by a reaction of Na 3-nitrobenzenesulfonate with phosphorus oxychloride in sulfolane (Chem. Abstr. 98 [1983] 215 331 t).

Finally, the desired 3-nitrobenzenesulfonyl chloride could also be obtained in a yield of about 90% (SU 1097613 [1982]) from the reaction of benzene with chlorosulfonic acid and a mixture of conc. nitric acid and conc. sulfuric acid.

There was therefore a need for an economically and ecologically advantageous process for the preparation of 3-nitrobenzenesulfonyl chloride in high yields.

It has now surprisingly been found that 3-nitrobenzenesulfonyl chloride can be advantageously prepared in high yields from nitrobenzene and chlorosulfonic acid by reacting nitrobenzene with chlorosulfonic acid at temperatures of about 90° to about 120° C. and allowing an inorganic acid chloride to act on the resulting reaction mixture at about 40° to about 90° C., preferably at about 60° to about 80° C.

In detail, the process is expediently carried out by initially introducing the chlorosulfonic acid at a temperature of about 90° to about 120° C., preferably of about 110° to about 115° C., and metering in the nitrobenzene. When the total amount of nitrobenzene has been added, the reaction mixture is advantageously kept for about a further 4 hours in the temperature ranges indicated and then allowed to cool to about 40° to about 90° C. The inorganic acid fluoride is then metered in in this temperature range, but preferably at about 60° to about 80° C. It is then advantageous to keep the reaction mixture for about a further 2 to 3 hours in this temperature range.

Phosphorus oxychloride, phosphorus trichloride or thionyl chloride, for example, can be employed as inorganic acid chlorides. Phosgene can also be used and should additionally be included by the term "inorganic acid chloride". The use of thionyl chloride is particularly preferred.

About 3.0 to about 10.0 mol, preferably about 3.5 to about 6.0 mol, particularly preferably about 4.0 to about 4.6 mol, of chlorosulfonic acid are employed in the process according to the invention per mol of nitrobenzene. If less than 3 mol of chlorosulfonic acid are used per mol of nitrobenzene, ranges are reached in which the reaction solution tends to decompose more easily. It is actually possible to employ more than 10 mol of chlorosulfonic acid, but less efficient, as in this case the excess of chlorosulfonic acid which has to be disposed of later only increases without noticeable advantage.

The process according to the invention includes the continuous procedure. It is achieved, for example, in a cascade of at least two kettles by allowing chlorosulfonic acid and nitrobenzene to run into the first kettle at a constant temperature of, for example, 110°–115° C. A desired mean residence time is set with the aid of an overflow. A temperature of, for example, 60°–80° C. is kept in a second kettle and the desired amount of inorganic acid chloride, for example thionyl chloride, is metered in. It is possible, but not absolutely necessary, to allow the reaction solution to subsequently react in a third kettle before working it up.

The cascade can be replaced by another continuously working apparatus, for example a recirculating reactor or a tube reactor.

The inorganic acid chloride is used in an amount of about 0.1 to about 5.0 mol, preferably of about 0.2 to about 1.0 mol, per mol of nitrobenzene.

The process according to the invention can be carried out either at normal pressure or at elevated pressure.

The desired 3-nitrobenzenesulfonyl chloride is obtained in a yield of about 95 to about 98% of theory with the aid of the process according to the invention. The high yield brings with it the further advantage that the waste water is virtually no longer polluted with nitrobenzene or nitrobenzenesulfonic acid.

The reaction mixtures obtained according to the invention surprisingly have a high thermal stability, as a result of which the safety of the reaction procedure is increased. Differential thermoanalysis shows that exothermic decomposition only sets in above 180° C.

3-Nitrobenzenesulfonyl chloride can be isolated by discharging the reaction mixture into ice-water and filtering off the precipitated product with suction. The crude product obtained is of high purity and can be employed without further purification.

The process according to the invention is illustrated by the example below, without being restricted thereto.

EXAMPLE 123.1 g (1.0 mol) of nitrobenzene was added dropwise at 112° C. to 521.0 g (4.4 mol) of chlorosulfonic acid over the course of 4 hours. The mixture was then stirred at this temperature for 4 hours. After it had been cooled to 70° C., 110.0 g (0.92 mol) of thionyl chloride were added dropwise over the course of 2 hours. The reaction mixture was then stirred at this temperature until evolution of gas had ended. It was then cooled and discharged at 5° C. into ice-water. The precipitated 3-nitrobenzenesulfonyl chloride was then filtered off with suction and washed with water and with sodium hydrogen carbonate. 237.5 g of moist 3-nitrobenzenesulfonyl chloride having a purity of 89.9% were obtained in this manner. The dry content was 213.5 g, which corresponds to a yield of 96.3%.

We claim:

1. A process for the preparation of 3-nitrobenzenesulfonyl chloride from nitrobenzene and chlorosulfonic acid, which comprises reacting nitrobenzene with chlorosulfonic acid at about 90° to about 120° C. and allowing thionyl chloride to act on the resulting reaction mixture at about 40° to about 90° C.

2. The process as claimed in claim 1, wherein the reaction of nitrobenzene with chlorosulfonic acid is carried out at about 110° to about 115° C.

3. The process as claimed in claim 1, wherein the subsequent treatment with the inorganic acid chloride is carried out at a temperature of about 60° to about 80° C.

4. The process as claimed in claim 1, wherein about 3.0 to about 10.0 mol of chlorosulfonic acid are employed per mol of nitrobenzene.

5. The process as claimed in claim 1, wherein about 3.5 to about 6.0 mol of chlorosulfonic acid are employed per mol of nitrobenzene.

6. The process as claimed in claim 1, wherein about 4.0 to about 4.6 mol of chlorosulfonic acid are employed per mol of nitrobenzene.

7. The process as claimed in claim 1, wherein about 0.1 to about 5.0 mol of inorganic acid chloride are employed per mol of nitrobenzene.

8. The process as claimed in claim 1, wherein about 0.2 to about 1.0 mol of inorganic acid chloride is employed per mol of nitrobenzene.

9. The process as claimed in claim 1, wherein the process is carried out batchwise or continuously.

10. The process as claimed in claim 1, wherein the process is carried out at normal pressure or elevated pressure.

11. The process as claimed in claim 2, wherein the subsequent treatment with the inorganic acid chloride is carried out at a temperature of about 60° to about 80° C.

12. The process as claimed in claim 11, wherein said inorganic acid chloride is thionyl chloride.

13. The process as claimed in claim 2, wherein said inorganic acid chloride is thionyl chloride.

14. The process as claimed in claim 2, wherein about 3 to about 10 mol of chlorosulfonic acid are employed per mol of nitrobenzene.

15. The process as claimed in claim 3, wherein about 3 to about 10 mol of chlorosulfonic acid are employed per mol of nitrobenzene.

16. The process as claimed in claim 2, wherein about 0.1 to about 5 mol of inorganic acid chloride are employed per mol of nitrobenzene.

17. The process as claimed in claim 3, wherein about 0.1 to about 5 mol of inorganic acid chloride are employed per mol of nitrobenzene.

* * * * *